US 6,685,917 B2

(12) United States Patent
Rosenthal et al.

(10) Patent No.: US 6,685,917 B2
(45) Date of Patent: Feb. 3, 2004

(54) TREATMENT OF MUCOSITIS

(75) Inventors: Gary J. Rosenthal, Louisville, CO (US); Jeffrey B. Etter, Boulder, CO (US); Timothy C. Rodell, Aspen, CO (US); Wren H. Schauer, Boulder, CO (US); Adrian Samaniego, Louisville, CO (US)

(73) Assignee: RxKinetix, Inc., Louisville, CO (US)

( * ) Notice: Subject to any disclaimer, the term of this patent is extended or adjusted under 35 U.S.C. 154(b) by 0 days.

(21) Appl. No.: 09/993,383

(22) Filed: Nov. 21, 2001

(65) Prior Publication Data

US 2002/0119104 A1 Aug. 29, 2002

Related U.S. Application Data

(63) Continuation-in-part of application No. 09/721,516, filed on Nov. 22, 2000.

(51) Int. Cl.$^7$ .......................... A61K 31/195; A61K 7/16
(52) U.S. Cl. ....................................................... 424/49
(58) Field of Search ...................................... 424/49–58

(56) References Cited

U.S. PATENT DOCUMENTS

| | | | | |
|---|---|---|---|---|
| 3,091,569 A | * | 5/1963 | Sheffner | 167/58 |
| 4,176,197 A | * | 11/1979 | Olson | 424/319 |
| 4,615,697 A | * | 10/1986 | Robinson | 604/890 |
| 4,708,965 A | * | 11/1987 | Morgan | 514/563 |
| 4,946,870 A | * | 8/1990 | Partain et al. | 514/777 |
| 5,061,729 A | * | 10/1991 | Kincses et al. | 514/562 |
| 5,221,722 A | * | 6/1993 | Sehm | 526/230.5 |
| 5,286,480 A | * | 2/1994 | Boggs et al. | 424/54 |
| 5,296,500 A | * | 3/1994 | Hillebrand | 514/562 |
| 5,300,494 A | | 4/1994 | Brode, II et al. | 514/55 |
| 5,358,705 A | | 10/1994 | Boggs et al. | 424/54 |
| 5,458,879 A | * | 10/1995 | Singh et al. | 424/410 |
| 5,472,704 A | * | 12/1995 | Santus et al. | 424/435 |
| 5,490,978 A | * | 2/1996 | Spaltro et al. | 424/49 |
| 5,635,489 A | | 6/1997 | Haley | 514/21 |
| 5,637,616 A | | 6/1997 | Sharpe et al. | 514/562 |
| 5,707,635 A | * | 1/1998 | Deckner et al. | 424/401 |
| 5,744,155 A | * | 4/1998 | Friedman et al. | 424/434 |
| 5,817,625 A | * | 10/1998 | Haley | 514/12 |
| 5,843,881 A | * | 12/1998 | Dubois et al. | 512/1 |
| 5,904,927 A | * | 5/1999 | Amiji | 424/422 |
| 5,939,485 A | * | 8/1999 | Bromberg et al. | 524/556 |
| 5,993,846 A | | 11/1999 | Friedman et al. | 424/434 |
| 6,013,632 A | * | 1/2000 | Jones et al. | 514/17 |
| 6,107,281 A | | 8/2000 | Jones et al. | 514/17 |
| 6,126,930 A | | 10/2000 | Dubois et al. | 424/73 |
| 6,150,472 A | * | 11/2000 | Engbers | 525/404 |
| 6,159,485 A | * | 12/2000 | Yu et al. | 424/401 |
| 6,207,703 B1 | | 3/2001 | Ponikau | 514/460 |
| 6,231,889 B1 | * | 5/2001 | Richardson et al. | 424/464 |
| 6,255,502 B1 | * | 7/2001 | Penkler et al. | 552/549 |
| 6,291,500 B2 | * | 9/2001 | Ponikau | 514/393 |
| 6,297,337 B1 | * | 10/2001 | Marchant et al. | 526/328 |
| 6,316,011 B1 | * | 11/2001 | Ron et al. | 424/401 |
| 6,319,513 B1 | * | 11/2001 | Dobrozsi | 424/434 |
| 6,350,785 B2 | * | 2/2002 | Gehlsen | 514/725 |
| 6,432,415 B1 | * | 8/2002 | Osborne et al. | 424/400 |
| 6,458,373 B1 | * | 10/2002 | Lambert et al. | 424/405 |
| 6,468,548 B1 | * | 10/2002 | Kis | 424/400 |
| 6,479,068 B1 | * | 11/2002 | Sherratt et al. | 424/434 |
| 6,503,955 B1 | * | 1/2003 | Dobrozsi | 514/772.4 |
| 6,565,895 B2 | * | 5/2003 | Goddard et al. | 424/653 |
| 2001/0018059 A1 | | 8/2001 | Gehlsen | 424/401 |
| 2001/0025027 A1 | | 9/2001 | Sonis | 514/18 |
| 2002/0013331 A1 | | 1/2002 | Williams et al. | 514/282 |
| 2002/0095001 A1 | | 7/2002 | Gehlsen | 514/725 |
| 2002/0168334 A1 | | 11/2002 | Jacob et al. | 424/78.31 |
| 2003/0064913 A1 | | 4/2003 | Sonis | 514/1 |

FOREIGN PATENT DOCUMENTS

| | | |
|---|---|---|
| WO | WO 01/74324 A1 | 10/2001 |
| WO | WO 02/36098 A1 | 5/2002 |

* cited by examiner

*Primary Examiner*—Shep K. Rose
(74) *Attorney, Agent, or Firm*—Marsh Fischmann & Breyfogle LLP

(57) ABSTRACT

This present invention provides a therapeutic composition for use in the treatment of mucositis and a method for using such a therapeutic composition. The therapeutic composition includes a pharmaceutical substance effective for treating mucositis formulated with a biocompatible polymer, such as a biocompatible reverse-thermal gelation polymer.

23 Claims, 1 Drawing Sheet

TREATMENT OF MUCOSITIS

CROSS-REFERENCE TO RELATED APPLICATIONS

This application is a continuation-in-part of U.S. patent application Ser. No. 09/721,516 filed Nov. 22, 2000, the entire contents of which are incorporated herein by reference as if set forth herein in full.

FIELD OF THE INVENTION

This invention relates to a therapeutic composition useful for treatment of mucositis and methods for using the therapeutic composition.

BACKGROUND OF THE INVENTION

Mucositis is a serious and often very painful disorder involving inflammation of the mucous membrane, with the inflammation often accompanied by infection and/or ulceration. Mucositis can occur at any of the different mucosal sites in the body. A nonlimiting list of examples of locations where mucositis can occur include mucosal sites in the oral cavity, esophagus, gastrointestinal tract, bladder, vagina, rectum, lung, nasal cavity, ear and orbita. Mucositis often develops as a side effect of cancer therapy, and especially as a side effect of chemotherapy and radiation therapy for the treatment of cancer. While cancerous cells are the primary targets of cancer therapies, other cell types can be damaged as well. Exposure to radiation and/or chemotherapeutics often results in significant disruption of cellular integrity in mucosal epithelium, leading to inflammation, infection and/or ulceration at mucosal sites.

As one example, oral mucositis (OM) is a painful and costly complication of some cancer therapies. The oral cavity is lined with mucosal epithelium, and exposure to radiation and/or chemotherapeutics results in the disruption of cellular integrity leading to the development of ulcerative lesions commonly referred to as oral mucositis. Oral mucositis is most prevalent in patient populations with head and neck malignancies being treated with radiation therapy. Oral mucositis usually occurs after the second week of radiation therapy, with severe symptoms usually resolving within six weeks following completion of therapy. It has been reported that this condition also affects approximately forty percent of patients undergoing chemotherapy, bone marrow transplantation or combinations thereof. Chemotherapeutic agents likely to cause oral mucositis include bleomycin, dactinomycin, doxorubicin, etoposide, floxuridine, 5-fluorouracil, hydroxyurea, methotrexate, mitomycin, vinblastine, vincristine, and vinorelbine. The risk of developing mucositis is markedly exacerbated when chemotherapeutic agents that typically produce mucosal toxicity are given in high doses, in frequent repetitive schedules, or in combination with ionizing irradiation (e.g., conditioning regimens prior to bone marrow transplant). The lesions induced by chemotherapeutic agents are clinically significant by about a week after treatment and the severity progresses to about day ten through twelve and begins to subside by day fourteen.

Oral mucositis appears to be a four-phase process: the primary phase is inflammatory/vascular in nature resulting in a cytokine release from the epithelium brought on by damage caused by radiation and/or chemotherapy. The second phase, referred to as the epithelial phase, is signaled by atrophy and ulceration of the mucosal epithelium. The third phase is defined as the ulcerative/bacterial phase represented by ulcerative lesions that are prone to bacterial infection further compromising the patients' immune system. These painful lesions often limit a patient's ability to eat and drink and in some cases require hospitalization. The presence of these lesions can also interrupt scheduled chemotherapy and/or radiation treatments. The last phase, the healing phase, is characterized by a proliferation and differentiation of epithelium as well as bacterial control.

Routine oral hygiene is extremely important in reducing the incidence and severity of mucositis. Oral hygiene methods include rinsing/irrigation and mechanical plaque removal. Although not entirely supported by controlled clinical trials, allopurinol mouthwash and vitamin E have been cited as agents that may decrease the severity of mucositis. Prophylaxis against fungal infections is commonly employed in an effort to treat oral mucositis and includes use of topical antifungal agents such as nystatin-containing mouthwashes and clotrimazole troches. Although topical antifungal prophylaxis and treatment may clear superficial oropharyngeal infections, topical agents tend not to be well absorbed and have not been demonstrated to be effective against more deeply invasive fungal infections, which typically involve the esophagus and lower gastrointestinal tract. For this reason, systemic agents are indicated for treating all except superficial fungal infections in the oral cavity.

Many different compounds have been evaluated for use as a prophylaxis and treatment of oral mucositis. Current therapies include cryotherapy (ice chips) to reduce pain and inflammation, analgesics to manage pain, and antibiotic therapy to control the opportunistic infection. Analgesics such as lidocaine mouthwashes are effective for short periods of time but within hours the pain and discomfort usually returns.

Chlorhexidine is a broad spectrum antimicrobial with activity against gram-positive and gram-negative organisms, yeast, and other fungal organisms. It also has the desirable properties of sustained binding to oral surfaces and minimal gastrointestinal (GI) absorption, thereby limiting adverse systemic effects. Its use in the prophylaxis of oral infections shows promise in reducing inflammation and ulceration, as well as in reducing oral microorganisms in high-risk patient groups. Other agents, such as allopurinol, leucovorin, vitamins, and growth factors, have been tried for the prevention of chemotherapy-induced mucositis. Use of a capsaicin-containing candy has also been advocated to desensitize pain receptors in the mouth. Also, studies utilizing nonsteroidal agents and coating agents, such as sucralfate (Carafate), have had conflicting results. Finally, claims that chlorhexidine (Peridex) reduces mucositis in both irradiated patients and leukemia patients receiving bone marrow transplants have not been verified. To date, none of these approaches has shown a significant impact.

Occurrence of mucositis at mucosal sites other than in the oral cavity in association with chemotherapy or radiation therapy are mechanistically similar to the occurrence of oral mucositis. For example, patients undergoing radiation therapy treatment for non-small cell lung cancer frequently develop esophagitis as a side effect of treatment. Esophagitis in this patient population can impede the progress of cancer treatment.

Given that a large number of patients suffer mucositis annually and patients undergoing cancer therapy often receive multiple cycles of chemotherapy and/or radiation therapy, there is a significant need for improved treatment of mucositis. The present invention is directed to this need.

SUMMARY OF THE INVENTION

In one aspect, the present invention provides a therapeutic composition for the treatment of mucositis. By treatment of mucositis, it is meant that the therapeutic composition is effective to prevent or reduce the incidence, severity and/or duration of the disease. The therapeutic composition comprises at least one pharmaceutical substance that, as formulated in the therapeutic composition, presents therapeutic effect in mammalian hosts, typically human hosts, for the treatment of mucositis, together with at least one biocompatible polymer that aids delivery of the pharmaceutical substance to the targeted mucosal site. One preferred embodiment of the therapeutic composition includes N-acetylcysteine as the pharmaceutical substance and a polyoxyalkylene block copolymer as the biocompatible polymer.

The therapeutic composition can be made with or without reverse-thermal viscosity behavior. For many applications, reverse-thermal viscosity behavior is beneficial to permit administration in a lower viscosity fluid form that tends to convert to a higher viscosity form following administration as the temperature of the therapeutic composition increases in the body. This also facilitates administration at a refrigerated temperature, which is soothing and refreshing to the host in a number of situations, such as for the treatment of mucosal surfaces in the oral cavity or esophagus. The biocompatible polymer will often be a reverse-thermal gelation polymer capable of imparting the desired reverse-thermal viscosity behavior to the therapeutic composition. Also, the therapeutic composition can be made in a variety of product forms, with different product forms being more desirable for targeting treatment to different mucosal sites. Also, in some applications it is desirable that the reverse-thermal viscosity behavior can include reverse-thermal gelation, in which case the therapeutic composition converts to a gel form as the temperature of the composition is increased from below to above a reverse-thermal gel transition temperature. When the therapeutic composition has reverse-thermal gelation properties, the therapeutic composition will preferably have a reverse-thermal gel transition temperature that is no higher than, and even more preferably lower than, the physiological temperature of the host. Depending upon the specific application, the therapeutic composition could be administered to the host at a cold temperature at which the therapeutic composition is in the form of a flowable medium, or at a temperature at which the therapeutic composition is in the form of a gel. When administered in the form of a gel, the therapeutic composition will often have a thick, pudding-like texture. Inside the body, the gel tends to break down as biological fluids dilute the therapeutic composition. But even with breakdown of the gel, significant amounts of the biocompatible polymer and pharmaceutical substance tend to adhere to mucosal surfaces to promote effective delivery of the pharmaceutical substance to treat the targeted mucosal site.

When treating for oral mucositis, the therapeutic composition is preferably administered in the form of a flowable medium with sufficient fluidity for use as a mouthwash that can be swished in the oral cavity to promote adhesion of the biocompatible polymer, and therefore also the pharmaceutical substance, to mucosal surfaces in the oral cavity. The therapeutic composition will typically include a carrier liquid (also referred to herein as a liquid vehicle), such as water, and the pharmaceutical substance and the biocompatible polymer are each dissolved or suspended in the carrier liquid when the therapeutic composition is in the flowable medium form for introduction into the oral cavity.

When treating for esophagitis, the composition will preferably have a very high viscosity as it is swallowed to promote a long residence time in the esophagus and effective coating of mucosal surfaces in the esophagus. In one embodiment, the therapeutic composition is in a thick, pudding-like form, typically a gel form, that can be spooned into the mouth and swallowed. In another preferred embodiment, the therapeutic composition is introduced into the oral cavity as a flowable medium that undergoes a viscosity increase as it warms and is swallowed. For esophageal applications, when the therapeutic composition is administered as a cold flowable medium, the therapeutic composition preferably has reverse-thermal gelation properties.

For targeting mucosal surfaces in the stomach, the therapeutic composition will preferably be in a form so that it can be readily swallowed to coat the mucosal surfaces in the stomach. Preferred embodiments include those noted for treatment of esophagitis.

For application to nasal mucosal surfaces, it is preferred that the therapeutic composition be sufficiently fluid so as to be nebulizable or otherwise sprayable to generate a nasal spray of the therapeutic composition that can be introduced into the nasal cavity. Preferably, the therapeutic composition is at a refrigerated temperature when sprayed and exhibits reverse-thermal viscosity behavior, so that it undergoes an increase in viscosity as it warms in the nasal cavity, thereby promoting adhesion to mucosal surfaces. For nasal applications, it is preferred that the therapeutic composition have reverse-thermal gelation properties.

For application to ocular mucosal surfaces, it is preferred that the therapeutic composition be sufficiently fluid to be administratable in the form of eye-drops, but the therapeutic composition should preferably not gel following administration of the eye drops.

For application to rectal or vaginal mucosal surfaces, the therapeutic composition is preferably in the form of a viscous gel when at physiological temperature. The therapeutic composition can be formulated to exhibit reverse-thermal viscosity behavior so that it is administrable in a refrigerated form at a lower viscosity and converts to a higher viscosity form, preferably a gel form, as the therapeutic composition warms following administration.

For application to pulmonary mucosal surfaces, the therapeutic composition should be sufficiently fluid immediately prior to administration to permit the therapeutic composition to be aerosolized, such as by a nebulizer, for administration by inhalation of the therapeutic composition in aerosol form.

For enhanced performance of the therapeutic composition, it is important that one or more of the components of the therapeutic composition are sufficiently bioadhesive to promote ready adhesion to mucosal surfaces, thereby promoting retention of the pharmaceutical substance adjacent the mucosal surface for effective delivery to the targeted mucosal site. In one preferred embodiment, the biocompatible polymer is bioadhesive, so that when the therapeutic composition is contacted with a mucosal surface, at least a portion of the biocompatible polymer readily adheres to the surface. Preferably, the biocompatible polymer and the pharmaceutical substance are closely associated with each other in the therapeutic composition such that when the biocompatible polymer adheres to a surface inside the oral cavity, the pharmaceutical substance also adheres to the surface along with the biocompatible polymer. This will often be the case when the carrier liquid is water and the biocompatible polymer has surfactant properties. In a preferred embodiment the surfactant properties of the biocompatible polymer enhance solubility of the pharmaceutical substance in the carrier liquid. In one embodiment, the therapeutic composition includes, in addition to the biocompatible polymer, a separate bioadhesive agent that enhances the bioadhesive properties of the therapeutic composition. The bioadhesive agent is frequently a second polymer having even greater bioadhesive properties.

In a further enhancement, the therapeutic composition may include a penetration enhancer, which aids rapid transport of the pharmaceutical substance across the mucosal epithelium. The therapeutic composition can also include other components that are compatible with the pharmaceutical substance and the biocompatible polymer.

In another aspect, the invention involves a therapeutic composition useful for treatment of mucositis at a mucosal site, with the composition comprising a sulfur-containing antioxidant. Such sulfur-containing anti-oxidants include those in which the sulfur is preferably present in a thiol, thioether, thioester, thiourea, thiocarbamate, disulfide, or sulfonium group. A particularly preferred sulfur-containing antioxidant is N-acetylcysteine.

In another aspect, the present invention involves use of the therapeutic composition, in any form and with any formulation, for treatment of mucositis.

In another aspect, a method is provided for delivering to a mucosal site a pharmaceutical substance for treatment of mucositis at a mucosal site, involving introduction into a host of a therapeutic composition of the invention. In one embodiment, the method involves introducing a therapeutic composition into the host, with the therapeutic composition comprising the pharmaceutical substance and a biocompatible polymer. After the therapeutic composition is introduced into the host, at least a portion of the biocompatible polymer and the pharmaceutical substance adhere to a mucosal surface at the mucosal site.

Both the foregoing general description and the following detailed description are exemplary and explanatory and are intended to provide explanation of the invention as claimed. Other objects, advantages and novel features will be readily apparent to those skilled in the art from the following detailed description of the invention.

DETAILED DESCRIPTION OF THE INVENTION

Figure 1:
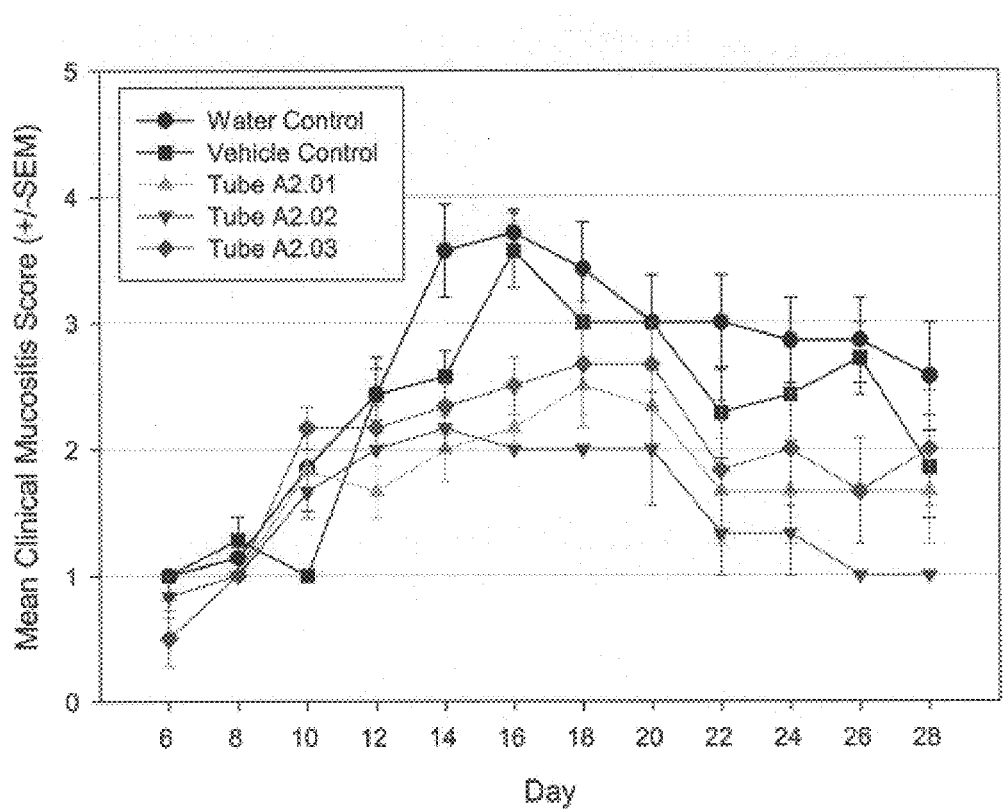
FIG. 1 is a plot of the clinical mucositis scores in the hamster buccal pouch following acute radiation and application of antioxidant-containing formulations. The various formulations (described in Table 1) were applied topically to the buccal pouch of Golden Syrian hamsters for 30 days. One day after beginning the application the buccal pouch was irradiated with one acute dose of radiation. The pouch was examined for mucositis by visually inspecting the pouch and scored for clinical mucositis.

As used herein, "NAC" means N-acetylcysteine.

As used herein, "biocompatible" means not having toxic or injurious effects on biological function in humans.

As used herein, "bioadhesive" means having the ability to adhere to a biological surface such as mucous membranes or other tissues for an extended period of time.

As used herein, "transition temperature" or "gel transition temperature" refers to a temperature at which a material, such as the biocompatible polymer or the therapeutic composition as the case may be, changes physical form from a liquid to a gel, or vice versa.

As used herein, "reverse-thermal gel transition temperature" refers to a temperature at which a material, such as the biocompatible polymer or the therapeutic composition as the case may be, changes physical form from a liquid to a gel as the temperature is increased from below to above the temperature, and changes physical form from a gel to a liquid as the temperature is decreased from above to below the temperature.

As used herein, "thermal gelation property" refers to a property of a material, such as the biocompatible polymer or the therapeutic composition, as the case may be, to change physical form from a liquid to a gel, or vice versa, due to a change in temperature.

As used herein, "reverse-thermal gelation property" refers to a property of a material, such as the biocompatible polymer or the therapeutic composition, as the case may be, to change physical form from a liquid to a gel with increasing temperature.

In one aspect, the present invention provides a therapeutic composition for delivery of mucositis therapeutics to humans, especially for use when bioadhesion and permeability of the oral mucositis therapeutic(s) are desired. The composition comprises at least one, and optionally more than one, mucositis therapeutic and a biocompatible polymer. Each mucositis therapeutic is a pharmaceutical substance that provides a therapeutic effect for at least one of prevention of mucositis and treatment of mucositis, either alone or in combination with other materials. In that regard, the therapeutic effect may be due to the direct action of the pharmaceutical substance of the composition, or may be due to one or more other materials activated by the pharmaceutical substance or for which the pharmaceutical substance is a precursor.

Nonlimiting examples of mucositis therapeutics useful in the present invention include antioxidants, antibacterials, antiinflammatories, anesthetics, analgesics, proteins, peptides, and cytokines, with antioxidants being particularly preferred. Optionally, the composition can also comprise a permeability enhancer and/or an active agent in addition to the oral mucositis agent(s). The composition can also include other components to the extent that the presence of the other components is not inconsistent with performance objectives of the composition.

The amount of mucositis therapeutic in the therapeutic composition of the present invention varies depending on the nature and potency of the therapeutic. In most situations, however, the amount of oral mucositis therapeutic in the composition will be less than about 20% w/w relative to the total weight of the therapeutic composition.

The therapeutic composition of the present invention provides a delivery system for bioadhesion, permeation, or prolonged and sustained action, of the oral mucositis therapeutic, thereby improving the efficacy of the oral mucositis therapeutic upon topical application to mucosal surfaces, a route that may otherwise be an ineffective means of therapy. Furthermore, the delivery system may reduce the frequency and duration of administration of the mucositis therapeutic as part of a treatment.

Not to be bound by theory but to aid in the understanding of the invention, it is believed that the therapeutic composition of the present invention improves bioadhesion onto and permeation into the mucosa, thus allowing this therapeutic agent to exert its actions more efficaciously at the target mucosal site. In addition, it is believed that the therapeutic composition may reduce or eliminate degradation of the therapeutic agent, again increasing the effectiveness of the therapeutic agent. Stabilizing agents can be incorporated into the composition of the present invention thereby further minimizing the degradation of the mucositis therapeutic, which directly impacts the effectiveness of the agent for treating mucositis and the ability to store or transport the composition.

The therapeutic composition can be in any convenient physical form, but is often preferably in the form of a flowable fluid medium at the time of administration. For example, when treating for oral mucositis, the therapeutic composition is preferably sufficiently fluid in character that it can be accepted in the oral cavity and swished in the manner of a mouthwash. In this situation, the therapeutic composition will typically include as its largest constituent a carrier liquid to impart the flowable fluid properties to the therapeutic composition. In most instances the carrier liquid will be water. The biocompatible polymer and mucositis therapeutic are each dissolved in the carrier liquid or suspended in the carrier liquid as a disperse phase. For example, the therapeutic composition can comprise an aqueous solution of the biocompatible polymer, with the mucositis therapeutic also dissolved in the solution and/or suspended as a precipitate in the solution. Preferably, both of the biocompatible polymer and the mucositis therapeutic are dissolved in the carrier liquid, at least at a temperature at which the therapeutic composition is to be administered to patients. Having the biocompatible polymer and the mucositis therapeutic codissolved in the carrier liquid ensures intimate mixing of the two materials, which promotes adhesion of the mucositis therapeutic to surfaces of the oral cavity along with the biocompatible polymer, thereby effectively using the therapeutic.

Proper selection of the biocompatible polymer is important to enhanced performance of therapeutic composition. In one important embodiment, the biocompatible polymer is selected so that when the biocompatible polymer is incorporated into the therapeutic composition, the rheology of the therapeutic composition is such that the viscosity of the therapeutic composition increases with increasing temperature in the vicinity of physiological temperature, which is typically about 37° C. In this way, the therapeutic composition can be administered as a lower viscosity flowable fluid medium at a cool temperature, and the viscosity of the therapeutic composition will increase as the therapeutic composition is warmed to physiological temperature. In one preferred embodiment for many applications when it is desirable for thetherapeutic composition to exhibit reverse-thermal viscosity behavior, the therapeutic composition exhibits reverse-thermal viscosity behavior over at least some range of temperatures between 1° C. and the physiological temperature of the host (e.g., 37° C. for a human host), and preferably over some range of temperatures between 1° C. and 20° C. The therapeutic composition can then be administered to the host in a lower viscosity form at a reduced temperature, typically lower than 20° C. and more typically form 1° C. to 20° C. Often a refrigerated temperature of from 1° C. to 10° C. and more often a refrigerated temperature of from 2° C. to 8° C. will be used. For example, the therapeutic composition may be introduced into the oral cavity at a temperature of from about 1° C. to about 20° C., and more preferably a temperature of from about 1° C. to about 10° C.

Nonlimiting examples of biocompatible polymers that can be used to make therapeutic composition of the present invention include polyethers (preferably polyoxyalkylene block copolymers, with more preferred polyoxyalkylene block copolymers including polyoxyethylene-polyoxypropylene block copolymers, referred to herein as POE-POP block copolymers, such as Pluronic® F68, Pluronic® F127, Pluronic® L121, and Pluronic® L101, and Tetronic® T1501); cellulosic polymers (including hydroxypropylmethyl cellulose, hydroxymethyl cellulose, hydroxypropyl cellulose, methyl cellulose and ethylhydroxyethyl cellulose); gelatin; polyethylene glycol; polyacrylic acid (such as Carbopol® gel); polyoxyl-35-castor oil (Cremophor® EL); and glycerol (glycerin). Pluronic®, Tetronic® and Cremophor® are trademarks of BASF Corporation. Carbopol® is a trademark of B. F. Goodrich. Furthermore, more than one of these exemplary biocompatible polymers may be included in the composition to provide the desired characteristics and other biocompatible polymers or other additives may also be included in the composition to the extent the inclusion is not inconsistent with performance requirements of the composition.

Particularly preferred biocompatible polymers, when the composition is to be administered with the biocompatible polymer in solution form dissolved in a solvent, include cellulosic polymers, glycerin, polyethylene glycol and polyoxyalkylene block copolymers.

Reverse-thermal gelation polymers are especially useful for imparting desirable rheological properties to the therapeutic composition. These biocompatible reverse-thermal gelation polymers can be incorporated into the therapeutic composition at concentrations so that the therapeutic composition has reverse-thermal gelation properties, or can be incorporated into the therapeutic composition at a concentration that does not impart reverse-thermal gelation properties to the therapeutic composition, but otherwise provides desired viscosity behavior for a particular application.

As used herein, the terms "reverse-thermal viscosity property" and "reverse-thermal viscosity behavior" each refer to a property of a component or components, and in particular a biocompatible polymer/water combination, to undergo a viscosity increase with increasing temperature across at least some temperature range. A reverse-thermal gelation property is a one type of reverse-thermal viscosity behavior in which a component or components, and in particular a biocompatible polymer/water combination in the therapeutic composition, change from a liquid form to a gel form as the temperature is raised from below to above a reverse-thermal gel transition temperature. "Reverse-thermal gelation polymer" refers to a polymercapable of interacting with a liquid vehicle, and particularly water, so that the polymer/liquidvehicle combination exhibits a reverse-thermal gelation property when the polymer and liquid vehicle are combined in at least some proportion. It should be appreciated that, if desired, a reverse-thermal gelation polymer and water can be incorporated into the therapeutic composition in such proportions that the therapeutic composition does not have a reverse-thermal gelation property, or does not even exhibit any reverse-thermal viscosity behavior. For most situations,however, the presence of reverse-thermal viscosity behavior is preferred.

With reverse-thermal viscosity behavior (which may or may not involve reverse-thermal gelation), the therapeutic composition can be administered to a patient at a cool temperature, as noted above, which provides a beneficial 'cold' feeling upon tissue, such as in the oral cavity or esophagus, of the host following administration. Also the therapeutic composition tends to become more viscous, and possibly even gelatinous depending upon the concentration of biocompatible polymer used, as the therapeutic composition warms to physiological temperature, depending upon the rapidity with which the therapeutic composition is diluted by biological fluids. Such reverse-thermal viscosity behavior does tend to promote greater bioadhesion of the biocompatible polymer and the pharmaceutical substance onto mucosal surfaces, leading to longer contact time of the pharmaceutical substance at the targeted mucosal site.

Furthermore, the biocompatible polymer and other components of the therapeutic composition may aid in the permeation of a mucosal therapeutic into the mucosa. For example, permeation into the oral mucosa or across oral mucosal cell membranes may aid in placing the therapeutic agent at additional target sites as well as provide for sustained action of the therapeutic agent within the oral mucosa.

Non-limiting examples of some biocompatible reverse-thermal gelation polymers include certain polyethers (preferably polyoxyalkylene block copolymers with more preferred polyoxyalkylene block copolymers including polyoxyethylene-polyoxypropylene block copolymers referred to herein as POE-POP block copolymers, such as Pluronic™ F68, Pluronic™ F127, Pluronic™ L121, and Pluronic™ L101, and Tetronic™ T1501); certain cellulosic polymers, such as ethylhydroxyethyl cellulose; and certain poly(ether-ester) block copolymers (such as those disclosed in U.S. Pat. No. 5,702,717, the entire contents of which are incorporated by reference herein as if set forth herein in full). Pluronic™ and Tetronic™ are trademarks of BASF Corporation. Furthermore, more than one of these and/or other biocompatible polymers may be included in the therapeutic composition. Also, other polymers and/or other additives may also be included in the therapeutic composition to the extent the inclusion is not inconsistent with the desired characteristics of the therapeutic composition. Furthermore, these polymers may be mixed with other polymers or other additives, such as sugars, to vary the transition temperature, typically in aqueous solutions, at which reverse-thermal gelation occurs.

As will be appreciated, any number of biocompatible polymers may now or hereafter exist that are capable of being used in the therapeutic composition, and such polymers are specifically intended to be within the scope of the present invention when incorporated into the therapeutic composition.

Polyoxyalkylene block copolymers are particularly preferred as biocompatible polymers for use in the therapeutic composition. A polyoxyalkylene block copolymer is a polymer including at least one block (i.e. polymer segment) of a first polyoxyalkylene and at least one block of a second polyoxyalkylene, although other blocks may be present as well. POE-POP block copolymers are one class of preferred polyoxyalkylene block copolymers for use as the biocompatible reverse-thermal gelation polymer in the formulated biocompatible polymer. POE-POP block copolymers include at least one block of a polyoxyethylene and at least one block of a polyoxypropylene, although other blocks may be present as well. The polyoxyethylene block may generally be represented by the formula $(C_2H_4O)_b$ when b is an integer. The polyoxypropylene block may generally be represented by the formula $(C_3H_6O)_a$ when a is an integer. The polyoxypropylene block could be for example $(CH_2CH_2CH_2O)_a$, or could be

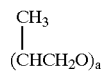

Several POE-POP block copolymers are known to exhibit reverse-thermal gelation properties, and these polymers are particularly preferred for imparting reverse-thermal viscosity and/or reverse-thermal gelation properties to the therapeutic composition. Examples of POE-POP block copolymers include Pluronic™ F68, Pluronic™ F127, Pluronic™ L121, Pluronic™ L101, and Tetronic™ T1501. Tetronic™ T1501 is one example of a POE-POP block copolymer having at least one polymer segment in addition to the polyoxyethylene and polyoxypropylene segments. Tetronic™ T1501 is reported by BASF Corporation to be a block copolymer including polymer segments, or blocks, of ethylene oxide, propylene oxide and ethylene diamine.

Some preferred POE-POP block copolymers have the formula:

$$HO(C_2H_4O)_b(C_3H_6O)_a(C_2H_4O)_bH \qquad I$$

which, in the preferred embodiment, has the property of being liquid at ambient or lower temperatures and existing as a semi-solid gel at mammalian body temperatures wherein a and b are integers in the range of 15 to 80 and 50 to 150, respectively. A particularly preferred POE-POP block copolymer for use with the present invention has the following formula:

$$HO(CH_2CH_2O)_b(CH_2(CH_3)CHO)_a(CH_2CH_2O)_bH \qquad II$$

wherein a and b are integers such that the hydrophobe base represented by $(CH_2(CH_3)CHO)_a$ has a molecular weight of about 4,000, as determined by hydroxyl number; the polyoxyethylene chain constituting about 70 percent of the total number of monomeric units in the molecule and where the copolymer has an average molecular weight of about 12,600. Pluronic™ F-127, also known as Poloxamer 407, is such a material. In addition, a structurally similar Pluronic™ F-68 may also be used.

The procedures used to prepare aqueous solutions which form gels or viscous solutions of polyoxyalkylene block copolymer are well known and are disclosed in U.S. Pat. No. 5,861,174, which is incorporated herein by reference in its entirety. When the therapeutic composition exhibits reverse-thermal gelation properties, the amount of biocompatible polymer and the amount of oral mucositis therapeutic agent are typically selected such that the resulting composition has a reverse-thermal gel transition temperature that is not higher than the physiological temperature of the host (e.g., 37° C. for human hosts). In most situations, the reverse-thermal gel transition temperature will be in a range having a lower limit of about 1°, more typically about 10° C., sometimes about 20° C. and sometimes even 25° C., and having an upper limit typically of about 40° C., more typically about 37° C. and even more typically about 25° C. Particularly preferred when the therapeutic composition has reverse-thermal gelation properties is for the reverse-thermal gel transition temperature to be in a range of from about 10° C. to about 25° C. In this situation, the reverse-thermal polymer/liquid vehicle combination will be in a liquid form when stored at normal refrigeration storage temperatures of 2° C. to 8° C.

As noted previously, in a preferred embodiment, at least the biocompatible polymer is dissolved in the carrier liquid in the therapeutic composition when the therapeutic composition is in a flowable medium form. With many of the biocompatible polymers useful with the present invention, however, at least some of the polymer will often come out of solution as the therapeutic composition is warmed in the after introduction into the host. This is often, but not always, the case, for example, when the therapeutic composition exhibits a reverse-thermal gel transition temperature at physiological temperature or lower. In some instances, the therapeutic composition is diluted by saliva in the oral cavity, or other by other biological fluids at other mucosal sites, at such a fast rate and to such an extent so as to entirely prevent gelling from occurring. However, even when gelling does not occur, some of the biocompatible polymer and mucosal therapeutic polymer will adhere to mucosal surfaces. When the therapeutic composition has the property of increasing viscosity with increasing temperature, as discussed above, the increasing viscosity may be accompanied, to some degree, by reduced solubility of the biocompatible polymer in the carrier liquid, which further promotes good adhesion to mucosal surfaces. In most situations, the biocompatible polymer will be substantially entirely dissolved in the carrier liquid when the temperature of the composition is at a temperature of about 5° C. There are, however, some situations where it may be desirable to have the therapeutic composition be in a gel form even at such low temperatures.

The concentration of the biocompatible polymer in the composition will vary depending upon the specific biocompatible polymer and the specific situation. In most situations, however, the biocompatible polymer will comprise from about 1% by weight to about 70% by weight, and more typically from about 5% by weight to about 20% by weight of the therapeutic composition. For example, particularly preferred for use of Pluronic® F-127 in many applications is a range of from about 10% by weight to about 20% by weight of the therapeutic composition.

The therapeutic composition of the present invention can also comprise other additives, including polymer or therapeutic agent stabilizers including sucrose, salts, and pH adjusting agents; preservatives including antioxidants such as butylated hydroxytoluene, antifungals, and antibacterials; and taste masking components. Inclusion of taste masking components is particularly desirable when administration is in the oral cavity, such as for treatment of oral mucositis or esophagitis. Nonlimiting examples of taste masking components include fruit flavorings (and particularly citrus flavorings), mint flavorings, salt, or sugars. In one preferred embodiment, the taste masking component imparts a citrus flavor, and preferably lemon flavor to the composition, such as when the taste masking component comprises lemon juice or a lemon extract.

The therapeutic composition of the present invention can also include a penetration enhancer. As used herein, a penetration enhancer is any material that, when added to a formulation including an active agent (such as the mucositis therapeutic in the therapeutic composition) enables permeation of the active agent across biological tissues and cells, such as epithelium, thereby increasing the amount of therapeutic at the target site. While the penetration enhancer may also act as a mucositis therapeutic or bioadhesive, the primary purpose of adding the penetration enhancer is to increase the amount or the rate of permeation of the mucositis therapeutic into the mucosa. Exemplary penetration enhancers include various molecular weight chitosans and chitosan derivatives, such as N,O-carboxymethyl chitosan; fatty acids, such as lauric acid, lipoic acid, and those extracted from cod-liver oil, including palmitic and oleic acids; bile salts such as deoxycholate, glycolate, cholate, taurocholate, taurodeoxycholate, and glycodeoxycholate; polyoxyethylenesorbitan such as Tween® 20 and Tween® 80; sodium lauryl sulfate; polyoxyethylene-9-lauryl ether (Laureth®-9); EDTA; citric acid; salicylates; caprylic/capric glycerides; sodium caprylate; sodium caprate; sodium laurate; sodium glycyrrhetinate; dipotassium glycyrrhizinate; glycyrrhetinic acid hydrogen succinate, disodium salt (carbenoxolone®); acylcarnitines such as palmitoylcarnitine; cyclodextrin; and phospholipids, such as lysophosphatidylcholine. Preferably, the penetration enhancer is selected from the group consisting of chitosans, fatty acids, EDTA, and bile salts. More preferably, the penetration enhancer is selected from the group consisting of chitosans and fatty acids.

When present, the amount of penetration enhancer in the therapeutic composition of the present invention generally varies depending on the particular penetration enhancer used. Typically, however, the amount of penetration enhancer, when used, will be present in the therapeutic composition in an amount from about 0.001% by weight to about 10% by weight of the therapeutic composition, preferably from about 0.01% by weight to about 5% by weight, and more preferably from about 0.01% by weight to about 1.0% by weight. In one particular aspect of the present invention where chitosan is used as the penetration enhancer, the amount of chitosan present in the composition is from about 0.01% by weight to about 10% by weight, preferably from about 0.1% by weight to about 1% by weight, and more preferably from about 0.1% by weight to about 0.5% by weight.

The therapeutic composition of the present invention can also include a bioadhesive agent that is different than and in addition to the biocompatible polymer, to further aid in depositing and holding the mucosal therapeutic in the vicinity of the desired mucosal tissue for delivery. While the bioadhesive agent may also act as an mucositis therapeutic or penetration enhancer, the primary purpose of adding the bioadhesive agent is to increase the duration of contact between the composition and the mucosal tissue. Nonlimiting examples of bioadhesive materials include Pluronic® F127, Pluronic® F68, chitosans, salivary or intestinal mucin glycoproteins, trefoil peptides, hydroxypropylmethyl cellulose, and polycarbophils. Improved bioadhesion of the composition onto the mucosa lengthens the contact time of the therapeutic at its target site. It is believed that increased contact time enables the mucositis therapeutic to be more effective in preventing or reducing the severity or duration of mucositis by having a longer time of action or a longer time with which to permeate the mucosa. When such a separate bioadhesive polymer is included in the therapeutic composition, the therapeutic composition will include at least two polymers, with a first polymer being the biocompatible polymer as discussed above and the second polymer being a bioadhesive agent that is more bioadhesive than the first polymer.

When a bioadhesive agent is used, the amount of bioadhesive agent in the therapeutic composition will vary depending on the nature and potency of the bioadhesive agent. Typically, however, when included in the therapeutic composition, the amount of the bioadhesive agent is from about 0.01% by weight of the composition to about 70% by weight of the composition, more typically from about 0.1% by weight to about 50% by weight, and most typically from about 0.1% by weight to about 25% by weight.

Nonlimiting examples of mucositis therapeutics that may be used to make the therapeutic composition of the present invention include antioxidants, antibacterials, antiinflammatories, anesthetics, analgesics, proteins, peptides and cytokines, including those currently available or later developed. Preferably the mucositis therapeutic is selected from the group consisting of antioxidants. More preferably the antioxidant is selected from the group consisting of sulfur-containing antioxidants or vitamin antioxidants, with sulfur-containing antioxidants generally being more preferred. Even more preferably, the sulfur-containing antioxidant includes sulfur in at least one constituent group selected from thiol, thioether, thioester, thiourea, thiocarbamate, disulfide and sulfonium, with thiol-containing antioxidants (also referred to as sulfhydryl-containing antioxidants) being particularly preferred. Some examples of preferred thiol-containing antioxidants include N-acetylcysteine (NAC) and glutathione. Other examples of preferred sulfur-containing antioxidants include S-carboxymethylcysteine and methylmethionine sulfonium chloride.

In an especially preferred embodiment, the sulfur-containing antioxidants are precursors for biosynthesis of glutathione in the host, such as by providing cysteine or a precursor for cysteine for glutathione synthesis. In this way, the mucosal therapeutic promotes the production of glutathione. Examples of antioxidants that are precursors for glutathione biosynthesis include NAC, procysteine, lipoic acid, s-allyl cysteine, and methylmethionine sulfonium chloride. In one preferred embodiment the mucositis therapeutic is NAC.

Examples of vitamin antioxidants include vitamin E, vitamin E mimetics, vitamin E analogs, vitamin C, and vitamin A. Particularly preferred in the vitamin class of antioxidants are water soluble vitamin forms of vitamin E, including Trolox and vitamin E TGPS (d-α-tocopherol polyethylene glycol 1000 succinate).

The action and selection of the antioxidant are not limited by the above description as many antioxidants may have a multitude of actions and thus fall under several classes of antioxidants or several classes of therapeutic agents. For example, NAC may directly scavenge free radicals extracellularly and provide cysteine intracellularly as a precursor for intracellular scavenging of free radicals via glutathione biosynthesis and regulation of glutathione-dependent antioxidative enzymes. Another example includes curcumin, which, in addition to its antioxidative action, possesses anti-inflammatory and antiproliferative actions that are beneficial in preventing or alleviating the clinical course of oral mucositis. In addition to therapeutic action, the antioxidant selected may exert other beneficial effects as a component of the therapeutic composition including bioadhesion as in the case of lipid soluble forms of vitamin E and penetration enhancement as in the case of lipoic acid, curcumin, and vitamin E TGPS.

The amount of mucosal therapeutic included in the therapeutic composition of the present invention varies depending on the nature and potency of the particular therapeutic. Typically, however, the amount of mucosal therapeutic present in the therapeutic composition is in a range having a lower limit typically of about 0.001%, more typically about 0.01%, and even more typically about 0.1% by weight of the therapeutic composition, and having an upper limit of typically about 50%, more typically about 25%, and even more typically about 10% by weight of the therapeutic composition.

The therapeutic composition of the present invention may be administered to a host (patient) to achieve any desired effect in the clinical outcome of the targeted mucositis. Preferably the host is a mammal, and more preferably a human. The therapeutic composition can be administered in a variety of forms adapted to the chosen route of administration.

When treating for oral mucositis, the therapeutic composition is contacted with the oral mucosa in the oral cavity. Administration in this situation can include, for example, use of a mouthwash, spray, lollipop or other product form of the formulation. Preferably, the mode of administering the therapeutic composition for treating oral mucositis is a mouthwash which, after being swished in the mouth, may then be spit out or, more preferably, swallowed in order to coat both mucosal surfaces in the mouth and in the esophagus, as well as provide systemic effects upon gastrointestinal absorption.

The therapeutic composition is typically prepared in water or a saline solution. Under ordinary conditions of storage and use, these preparations can also contain a preservative to prevent the growth of microorganisms. For oral mucositis applications, the therapeutic composition typically is a fluid, i.e., in a liquid form, to the extent that it is palatable and thus, easily tolerated, by the often nauseous cancer patient. The therapeutic composition can be stable under the conditions of manufacture and storage and preferably preserved against the contaminating action of microorganisms such as bacteria and fungi. The carrier liquid can be a solvent of dispersion medium containing, for example, water, ethanol, polyol (e.g., glycerol, propylene glycol, and liquid polyethylene glycol, and the like), and suitable mixtures thereof. The proper fluidity can be maintained, for example, by maintaining the temperature of the therapeutic composition having reverse-thermal gelation properties below the transition temperature. The prevention of the action of microorganisms can be brought about by various antibacterial and antifungal agents, for example, parabens, chlorobutanol, phenol, sorbic acid, thimerosal, benzoic acid, alcohol, benzalkonium chloride and the like. In many cases, it will be preferable to include isotonic agents, e.g., sugars, phosphate buffers, sodium benzoate, sodium chloride, or mixtures thereof.

In many situations, it will be desirable for the therapeutic composition to be in the form of a flowable medium when introduced into the host for treatment of a mucosal site. This will often be the case for example for oral mucositis applications in which the therapeutic composition is to be administered as a refrigerated mouthwash. In one preferred embodiment, the therapeutic composition has a relatively low viscosity when the therapeutic composition is at a temperature for introduction into the host for treatment. In this embodiment, the viscosity of the therapeutic composition when introduced into the host is no larger than 60 cP (centipoises), and more preferably no larger than 50 cP. Because the therapeutic composition is typically administered at a reduced temperature, in this embodiment, the therapeutic composition will preferably have a viscosity at 2° C. of no larger than 60 cP and more preferably no larger than 50 cP. When the therapeutic composition exhibits reverse-thermal viscosity behavior, the viscosity of the therapeutic composition will preferably exhibit an increase in viscosity from a viscosity of no larger than 60 cP (and more preferably no larger than 50 cP) to a viscosity of at least 70 cP, or even 80 cp or more (and more preferably even larger) as the temperature of the therapeutic composition is increased over at least some range of temperatures between 1° C. and the physiological temperature of the host (e.g., 37° C. for a human host). When the therapeutic composition has reverse-thermal gelation properties, the viscosity will often increase to a level of 90 cp, or even 100 cP or more with an increase in temperature from below to above the reverse-thermal gel transition temperature.

In some situations when treating for oral mucositis, it will be desirable to specifically target sublingual mucosal surfaces. In this situation, the therapeutic composition can be sublingually placed, such as in the form of a tablet, patch or film. In one preferred sublingual application, the therapeutic composition is already in the form of a gel when sublingually placed, and the gel then dissipates as it is diluted with biological fluids. In this situation, the administered gel can have a thick, pudding-like texture and can be spooned or squeezed from a tube into the sublingual location. In this situation, when administered, the therapeutic composition will typically have a viscosity of at least 70 cP, and more typically a viscosity of at least 80 cP, at least 90 cP or even at least 100 cP.

For oral mucositis applications when the therapeutic composition has reverse-thermal gelation properties, the therapeutic composition can be used as a mouthwash at a temperature below the reverse-thermal gel transition temperature, whereupon the therapeutic composition will ordinarily become more viscous or even gelatinous as it warms inside the mouth. Not all aspects of the invention when treating for oral mucositis are so limited, however. For example, in some instances the therapeutic composition may not become more viscous or gelatinous inside the mouth of the host, but the biocompatible polymer will still provide some protection to the oral mucositis therapeutic and enable contact and permeation of the mucositis therapeutic within the oral mucosa.

Solutes can be incorporated into the therapeutic composition of the present invention to stabilize the mucositis therapeutic. Stabilizing solutes such as those that modify the pH of the therapeutic composition or a second antioxidant, may aid in protecting and stabilizing the therapeutic by keeping it in a reduced, thus active, form. Furthermore, pH modification, inclusion of an antioxidant (in addition to the mucositis therapeutic), or inclusion of a solute such as sucrose may not only aid in protecting and stabilizing the therapeutic, but also allow the biocompatible polymer to form solutions at suitable viscosities at lower concentrations than needed in water or buffer alone and/or to change the transition temperature at which thermal gelation occurs. Thus, the working range of biocompatible polymer concentration can be widened and the transition temperature modified.

It is known that in some cases a gel will not form when the concentration of polyoxyethelene-polyoxypropylene block copolymer in water or dilute buffer is outside a particular range, e.g., equal to or less than 15% by weight in water for Pluronic™ F127. However, by introducing therapeutic-stabilizing solutes, or other components, into the therapeutic composition of the present invention, the transition temperature may be manipulated, while also lowering the concentration of polyoxyethelene-polyoxypropylene block copolymer that is necessary to form a gel. Also, the presence of the mucosal therapeutic, a penetration enhancer and other additives, tend to alter the viscosity behavior of the therapeutic composition, often by lowering the concentration of the reverse-thermal gelation polymer required to impart reverse-thermal gelation properties to the therapeutic composition.

Much of the foregoing description has been primarily directed to the treatment of oral mucositis. It should be recognized, however, that the same principles discussed above are also generally applicable to treatment of mucosal disorders occurring in other regions of the body, with the product form of the therapeutic composition being modified for administration to the other targeted mucosal site. For example, the therapeutic composition of the present invention is applicable for the prevention and/or treatment of mucosal disorders of the esophagus, vagina, bladder and the entire gastrointestinal tract (for example including stomach, small intestine, large intestine and rectum). These mucosal disorders include but are not limited to sinusitis, asthma, inflammatory bowel disease, colitis, cystitis, GERD, proctitis, stomatitis, celiac disease and Crohn's disease. Mucosal disorders at these other locations are mechanistically similar to oral mucositis, and particularly when the disorder is the result of chemotherapy or radiation therapy. For example, patients undergoing radiation therapy treatment for non-small cell lung cancer frequently develop esophagitis as a side effect of treatment. Esophagitis in this patient population can impede the progress of cancer treatment. The pharmaceutical substances described above are also applicable for treatment of mucositis disorders in other regions of the body. The method of delivery to the affected region may be by any convenient technique as suitably adapted for the particular region of the body at issue.

Depending on the area of delivery the pharmaceutical substance of the present invention can be formulated in different product forms. Some examples of possible product forms for administration of the therapeutic composition include an oral solution, bladder irrigation solution, gel, slurry, mouthwash, lozenge, tablet, film, patch, lollipop, spray, drops or suppository. For example, a gel formulated into a suppository would be one preferred product form for administration to treat mucosal surfaces of either the rectum or the vagina. A tablet, patch or film could be formulated to administer the therapeutic composition sublingually. A slurry or oral solution could be used for treatment of mucosal surfaces in the oral cavity, esophagus and/or gastrointestinal tract. A bladder irrigation solution would be administered to the bladder by catheter. A spray would be advantageous in delivering the present invention to either the nasal cavity or the lungs, while a droplet formulation would be advantageous for delivery to the eye or inner ear.

When treating for esophagitis, the therapeutic composition could be introduced into the oral cavity in the form of a flowable medium, such as discussed above with respect to treatment for oral mucositis, with the therapeutic composition being swallowed to coat at least a portion of mucosal surfaces in the esophagus. The therapeutic composition could be immediately swallowed after introduction into the oral cavity, or could be swallowed after it has first been swished in the oral cavity. In one preferred embodiment, for treating esophagitis, the therapeutic composition is introduced into the oral cavity in a highly viscous form, typically a gel form, that may have a thick, pudding-like texture. When this highly viscous form is swallowed it moves slowly through the esophagus to promote good coating of esophageal mucosal surfaces. When introduced into the oral cavity of the host, the high viscosity form will be at a temperature where the viscosity of the therapeutic composition has a viscosity of at least 70 cP, often at least 80 cP, or even at least 90 cP or at least 100 cP or more. Also, because the coating effect to the esophageal mucosal surfaces must be accomplished with only a single pass through the esophagus, it is highly preferred that the therapeutic composition include a bioadhesive agent, as discussed above, with a preferred bioadhesive agent being a carbophil polymer.

When treating for mucositis in the gastrointestinal tract, and particularly in the stomach, the therapeutic composition will generally be administered to the oral cavity and swallowed as described with treatment of esophagitis. The product form of the therapeutic composition when introduced into the oral cavity will preferably be of a form as described with respect to treatment for esophagitis.

When treating for mucositis at a nasal mucosal site, the therapeutic composition is introduced into the nasal cavity to contact mucosal surfaces in the nasal cavity. For nasal applications, a preferred method of administration is in the form of a nasal spray, such as is generated by a nasal nebulizer or other spray device. Also, for nasal applications it is generally preferred that the therapeutic composition have reverse-thermal gelation properties, with a reverse-thermal gel transition temperature that is no higher than the physiological temperature of the host. When the spray is generated, the therapeutic composition should be at a temperature at which the therapeutic composition is in the form of a flowable medium that can be processed in the nebulizer or other spray device to generate the desired spray.

When treating for mucositis at a pulmonary mucosal site, the therapeutic composition is typically introduced into the host by inhalation of the therapeutic composition in aerosol form to introduce the therapeutic composition into at least one lung of the host. Considerations are similar to delivery of a nasal spray for nasal applications. For pulmonary applications, however, the aerosol should preferably have smaller and better controlled aerosol particle size, such as could be provided by a pulmonary nebulizer or other inhaler. Again, when generating the aerosol, the therapeutic composition should be at a temperature where the therapeutic composition is in the form of a flowable medium.

When treating for mucositis at a rectal mucosal site, the therapeutic composition will be introduced into the rectum of the host. Preferably, for rectal applications the therapeutic composition will be in the form of a gel at least when the therapeutic composition is at the physiological temperature of the host. The therapeutic composition may or may not have reverse-thermal gelation properties, but preferably does have reverse thermal gelation properties and is administrable as a flowable medium below the reverse-thermal gel transition temperature. Considerations for vaginal applications are similar to those for rectal applications, except that the therapeutic composition is introduced into the vagina rather than the rectum.

When treating for mucositis at a mucosal site in the bladder, the therapeutic composition will typically be introduced into the bladder through a catheter. In this situation, it is preferred that during administration, the therapeutic composition be in the form of a flowable medium that is injectable through the catheter. The therapeutic composition will preferably not have reverse-thermal gelation properties.

When treating for mucositis at an ocular mucosal site, the therapeutic composition is generally introduced into the orbita, preferably by applying to an eye of the host at least one drop of the therapeutic composition in the form of a flowable medium. The therapeutic composition will preferably not have reverse-thermal gelation properties.

When treating for mucositis at an aural mucosal site, the therapeutic composition is generally introduced into the ear, and preferably into the inner ear, by administration into the ear of at least one drop of the therapeutic composition in the form of a flowable medium. The therapeutic composition will preferably not have reverse-thermal gelation properties.

The following example is given to illustrate the present invention. It should be understood that the invention is not to be limited to the specific conditions or details described in the example.

EXAMPLE

This example describes the formulation and use of the antioxidant, NAC, within a Pluronic® F127 delivery matrix in the absence and presence of chitosan as a penetration enhancer, for preventing or reducing the clinical outcome of oral mucositis in a hamster model of radiation-induced buccal mucositis.

Preparation of Stock Solutions

Pluronic® F127 (poloxamer 407; BASF Corporation, Washington, N.J.) was autoclaved and dissolved in sterile water for injection (Abbott Laboratories, North Chicago, Ill.) at 30% (w/w). Chitosan (medium molecular weight; Sigma-Aldrich, St. Louis, Mo.) was autoclaved and dissolved at 3% (w/w) in sterile filtered water for injection containing 1% (v/v) acetic acid (Fisher Scientific, Fair Lawn, N.J.). NaOH (Fisher Scientific) was prepared in sterile water for injection at 4 M and sterile filtered.

Preparation of Antioxidant Formulations

The antioxidant, N-acetyl-L-cysteine (NAC; Sigma-Aldrich), was formulated in the various delivery matrices by weighing and mixing the desired components under sterile conditions. The pH was determined by litmus pH paper (Sigma-Aldrich). Examples of antioxidant-containing formulations are described below in Table 1.

TABLE 1

Descriptions of formulations

| Formulation | Antioxidant (Wt %) | Pluronic® F127 (Wt %) | Chitosan (Wt %) | NaOH (M) | pH |
|---|---|---|---|---|---|
| N-acetyl cysteine | | | | | |
| Tube A2.01 | 10 | 16.25 | 0.5 | 0.57 | 4–5 |
| Tube A2.02 | 10 | 16.25 | 0 | 0.57 | 4–5 |
| Tube A2.03 | 10 (in WFI) | 0 | 0 | 0.57 | 5–6 |
| Controls | | | | | |
| Vehicle control | 0 | 16.25 | 0.5 | 0 | 5–6 |
| Water control (WFI) | 0 | 0 | 0 | 0 | |

All formulations were stored at 2–8° C.

Use of Antioxidants in an Animal Model of Radiation-Induced Oral Mucositis

Study Location and Animals

The study was carried out by Biomodels and Affiliates (Boston, Mass.) at the Massachusetts College of Pharmacy and Health Sciences. Male Golden Syrian hamsters (Charles River Laboratories, Wilmington, Mass.), 5 to 6 weeks of age, weighing approximately 90 g at study commencement were used.

Radiation

The acute-radiation hamster model was developed by Dr. Steve Sonis (Harvard School of Dental Medicine, Brigham and Women's Hospital, Boston, Mass.). Hamsters were anesthetized with an intraperitoneal injection of sodium pentobarbital (80 mg/kg). The left buccal pouch was everted, fixed and isolated using a lead shield. Oral mucositis was induced using a standardized acute radiation protocol. A single dose of radiation (40 Gy/dose) was administered to all animals on Day 0. Radiation was generated with a 250 kilovolt potential (15-ma) source at a focal distance of 50 cm, hardened with a 0.35 mm Cu filtration system. Irradiation targeted the left buccal pouch mucosa at a rate of 121.5 cGy/minute. This radiation protocol produces 'peak' oral mucositis 14 to 18 days after irradiation.

Formulation Application

Each animal was dosed topically 3 times per day by applying 0.25 mL of formulation into the the left (irradiated) buccal pouch per application. Dosing was carried out from Day −1 to Day 28.

Mucositis Evaluation

Clinical mucositis was assessed every 2nd day starting on Day 6 to Day 28. Mucositis was evaluated by visual scoring using a validated photographic scale for comparison. Following visual scoring, a photograph of each animal's mucosa was taken so that mucositis could be scored 'blind' at the end of the study.

Mucositis Data

Data showing the results of visual scoring of mucositis to Day 28 are shown in FIG. 1. Values are the mean clinical mucositis scores±SEM per formulation treatment group (N=7 hamsters per group).

TABLE 2

Description of clinical mucositis scoring:

| Score: | Description: |
|---|---|
| 0 | Pouch completely healthy. No erythema or vasodilation |
| 1 | Light to severe erythema and vasodilation. No erosion of mucosa |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray due to pseudomembrane. Cumulative size of ulcers should equal about ¼ of the pouch. Severe erythema and vasodilation. |
| 4 | Cumulative size of ulcers should equal about ½ of the pouch. Loss of pliability. Severe erythema and vasodilation. |
| 5 | Virtually all of pouch is ulcerated. Loss of pliability (pouch can only partially be extracted from mouth) |

A score of 1–2 is considered to represent a mild stage of the disease, whereas a score of 3–5 is considered to indicate moderate to severe mucositis. Following visual scoring, a photograph was taken of each animal's mucosa using a standardized technique. At the conclusion of the experiment, all film was developed and the photographs randomly numbered. At least two independent trained observers graded the photographs in blinded fashion using the above-described scale (blinded scoring).

Clinical mucositis scores in the hamster buccal pouch following acute radiation and application of NAC-containing formulations. Values are the mean clinical mucositis scores±SEM per formulation treatment group (N=7 hamsters per group).

Results

The water control treatment group exhibited the expected clinical mucositis score (i.e., a score of 3 or 4) at the expected peak mucositis time (i.e., 14 to 18 days post-irradiation). All three NAC formulations reduced the mean clinical mucositis scores relative to the vehicle and water controls, with the NAC formulated in Pluronic® F127 (Tube A2.02) being the most effective. The vehicle appeared to have some beneficial effect in reducing the mean clinical mucositis score at day 14, but this effect was not maintained throughout the peak time of mucositis induction.

The description of the invention, including the foregoing example, has been presented for purposes of illustration and description. Moreover, the description is not intended to limit the variations and modifications commensurate with the above teachings, and the skill or knowledge in the relevant art are within the scope of the present invention. It will be apparent to those skilled in the art that various modifications and variations can be made in the methods and compositions of the present invention without departing from the spirit or scope of the present invention, and thus it is intended that the present invention cover modifications and variations of this invention provided they come within the scope of the appended claims and their equivalents. Also, the preferred embodiment(s) described hereinabove are intended to explain the best mode known of practicing the invention and to enable others skilled in the art to utilize the invention in various embodiments and with the various modifications required by their particular applications or uses of the invention. Moreover, to the extent that features are not functionally incompatible, it is contemplated within the scope of the present invention that any feature of any disclosed embodiment is combinable in any combination with any feature of any other embodiment. It is intended that the appended claims be construed to include alternate embodiments to the extent permitted by the prior art. Use of the terms "comprise," "include," "contain," "have" and variations of those terms are used to indicate the presence of an attribute, feature or component, but not to the exclusion of the presence of other possible attributes, features or components.

What is claimed is:

1. A method for treatment of oral mucositis in an oral cavity of a host as a side effect of the host undergoing cancer therapy treatment, the cancer therapy treatment comprising one or both of chemotherapy and radiation therapy, the method comprising:

introducing a therapeutic composition into the oral cavity of the host, the therapeutic composition comprising:
(i) a reverse-thermal gelation biocompatible polymer that is a polyoxyalkylene block copolymer, comprising at least one block of a first polyoxyalkylene and at least one block of a second polyoxyalkylene that is different than the first polyoxyalkylene;
(ii) a carrier liquid interacting with the biocompatible polymer to impart reverse-thermal viscosity behavior to the therapeutic composition; and
(iii) a pharmaceutical substance selected from the group consisting of glutathione and a precursor for glutathione biosynthesis, the pharmaceutical substance being effective for treating the oral mucositis at a mucosal site within the oral cavity;

wherein, during the introducing the therapeutic composition is at an administration temperature that is at least 1° C. and that is lower than the physiological temperature of the host, at the administration temperature the therapeutic composition being in the form of a solution comprising the pharmaceutical substance and the biocompatible polymer dissolved in the carrier liquid, and after the introducing, at least a portion of the biocompatible polymer and at least a portion of the pharmaceutical substance adhere to a mucosal surface at the mucosal site; and wherein, the therapeutic composition exhibits the reverse-thermal viscosity behavior over at least some range of temperatures between the administration temperature and the physiological temperature of the host.

2. The method of claim 1, wherein the pharmaceutical substance comprises a thiol-containing compound.

3. The method of claim 1, wherein the pharmaceutical substance comprises a sulfur-containing antioxidant.

4. The method of claim 1, wherein the pharmaceutical substance comprises a sulfur-containing antioxidant selected from the group consisting of S-carboxymethylcysteine, procysteine, lipoic acid, s-allyl cysteine, and methylmethionine sulfonium chloride.

5. The method of claim 4, wherein the sulfur-containing antioxidant includes sulfur in at least one functional group selected from the group consisting of thiol, thioether, thioester, thiourea, thiocarbamate, disulfide, and sulfonium salt.

6. The method of claim 1, wherein the pharmaceutical substance comprises a precursor for glutathione biosynthesis.

7. The method of claim 6, wherein the precursor is selected from the group consisting of procysteine, lipoic acid, s-allyl cysteine, and S-carboxymethylsysteine, and methylmethionine sulfonium chloride.

8. The method of claim 1, wherein the pharmaceutical substance is N-acetylcysteine.

9. The method of claim 1, wherein when the therapeutic composition exhibits an increase in viscosity from no larger than about 60 cP to at least about 70 cP when a temperature of the composition is increased from the administration temperature to the physiological temperature of the host.

10. The method of claim 1, wherein when the therapeutic composition exhibits an increase in viscosity from on larger than 50 cP to at least about 70 cP when a temperature of the composition is increased from the administration temperature to the physiological temperature of the host.

11. The method of claim 1, wherein the therapeutic composition has reverse-thermal gelation properties and a reverse-thermal liquid-gel transition temperature in a range of from the administration temperature to the physiological temperature of the host.

12. The method of claim 1, wherein the administration temperature is within a range of from 1° C. to 10° C.

13. The method of claim 1, wherein the therapeutic composition comprises a bioadhesive agent other than the biocompatible polymer.

14. The method of claim 1, wherein the therapeutic composition comprises a penetration enhancer.

15. The method of claim 1, wherein the therapeutic composition comprises reverse-thermal gelation behavior between the administration temperature and the physiological temperature of the host, and the method comprises, after the introducing, swishing the therapeutic composition in the mouth to promote adhesion of the biocompatible polymer and the pharmaceutical substance to the mucosal surface and retention of the pharmaceutical substance adjacent to the mucosal surface for permeation across the mucosal surface, and after the swishing, ejecting from the mouth at least a portion of remaining of the therapeutic composition.

16. The method of claim 1, wherein the therapeutic composition comprises from 0.1 to 20 weight percent of the pharmaceutical substance and from 5 to 20 weight percent of the biocompatible polymer.

17. The method of claim 16, wherein the first polyoxyalkylene is a polyoxyethylene and the second polyoxyalkylene is a polyoxypropylene.

18. The method of claim 17, wherein the biocompatible polymer comprises two of the block of the first polyoxyalkylene and one of the block of the second polyoxyalkylene.

19. The method of claim 16, wherein the therapeutic composition comprises up to 10 weight percent of the pharmaceutical substance.

20. The method of claim 19, wherein the pharmaceutical substance is N-acetylcysteine.

21. The method of claim 1, wherein the introducing occurs prior to the cancer therapy treatment.

22. The method of claim 1, wherein the introducing occurs multiple times, a first said introducing occurring prior the cancer therapy treatment a second said introducing occuring after the cancer therapy treatment.

23. The method of claim 22, wherein the host undergoes multiple cycles of the cancer therapy treatment.

* * * * *

UNITED STATES PATENT AND TRADEMARK OFFICE
CERTIFICATE OF CORRECTION

PATENT NO. : 6,685,917 B2
DATED : February 3, 2004
INVENTOR(S) : Rosenthal et al.

It is certified that error appears in the above-identified patent and that said Letters Patent is hereby corrected as shown below:

Column 7,
Line 49, delete the word "thetherapeutic", and insert therefor -- the therapeutic --.

Column 8,
Line 49, delete the word "liquidvehicle", and insert therefor -- liquid vehicle --;
Line 57, delete the word "situations,however,", and insert therefor -- situations, however, --.

Column 20,
Line 41, delete the word "physicological", and insert therefor -- physiological --.

Column 21,
Line 6, delete the word "S-carboxymethylsysteine", and insert therefor -- S-carboxymethylcysteine --;
Lines 10 and 15, delete the word "when";
Line 16, delete the word "on", and insert therefor -- no --.

Column 22,
Line 30, delete the word "occuring", and insert therefor -- occurring --.

Signed and Sealed this

Eleventh Day of May, 2004

JON W. DUDAS
*Acting Director of the United States Patent and Trademark Office*